(12) United States Patent
Tanaka et al.

(10) Patent No.: US 9,538,989 B2
(45) Date of Patent: Jan. 10, 2017

(54) ULTRASOUND IMAGING EQUIPMENT AND METHOD

(75) Inventors: Tomohiko Tanaka, Tokyo (JP); Kunio Hashiba, Tokyo (JP)

(73) Assignee: HITACHI, LTD., Tokyo (JP)

( * ) Notice: Subject to any disclaimer, the term of this patent is extended or adjusted under 35 U.S.C. 154(b) by 36 days.

(21) Appl. No.: 14/342,970

(22) PCT Filed: Aug. 1, 2012

(86) PCT No.: PCT/JP2012/069599
§ 371 (c)(1),
(2), (4) Date: Apr. 1, 2014

(87) PCT Pub. No.: WO2013/057999
PCT Pub. Date: Apr. 25, 2013

(65) Prior Publication Data
US 2014/0236008 A1    Aug. 21, 2014

(30) Foreign Application Priority Data

Oct. 20, 2011   (JP) .................................. 2011-231066

(51) Int. Cl.
*A61B 8/14*     (2006.01)
*A61B 8/08*     (2006.01)
(Continued)

(52) U.S. Cl.
CPC ............... *A61B 8/5223* (2013.01); *A61B 8/06* (2013.01); *A61B 8/488* (2013.01); *A61B 8/5207* (2013.01);
(Continued)

(58) Field of Classification Search
CPC ............. A61B 8/04; A61B 8/06; A61B 8/065; A61B 8/0883; A61B 8/0891; A61B 8/14; A61B 8/463; A61B 8/488; A61B 8/5207; A61B 8/5223

See application file for complete search history.

(56) References Cited

U.S. PATENT DOCUMENTS

| 4,913,159 | A | 4/1990 | Gardin et al. |
| 7,229,412 | B2 | 6/2007 | Jacob et al. |

(Continued)

FOREIGN PATENT DOCUMENTS

| JP | 3-021230 | 1/1991 |
| JP | 7-241289 A | 9/1995 |

(Continued)

OTHER PUBLICATIONS

International Preliminary Report on Patentability in corresponding application No. PCT/JP2012/069599 reported on May 13, 2014.

(Continued)

*Primary Examiner* — Mark Remaly
(74) *Attorney, Agent, or Firm* — Brundidge & Stanger, P.C.

(57) ABSTRACT

In ultrasonic imaging, a physically consistent value of blood flow velocity is measured in the vicinity of body tissues. The ultrasound imaging apparatus comprises a shape extraction part for recognizing shape data of biological tissues by using echo signals reflected from a test subject irradiated with ultrasonic waves, a flow velocity distribution acquisition part for detecting blood flow velocities in the vicinity of the tissues from the echo signals, and a velocity determination part for extracting velocity information desired by a tester (objective velocity information). The velocity determination part sets a model of the objective blood flow, and determines a velocity of actually measured velocity distribution consistent with velocity distribution estimated from the model.

15 Claims, 14 Drawing Sheets

(51) Int. Cl.
  *A61B 8/06* (2006.01)
  *A61B 8/04* (2006.01)
  *A61B 8/00* (2006.01)

(52) U.S. Cl.
  CPC .............. *A61B 8/04* (2013.01); *A61B 8/065* (2013.01); *A61B 8/0883* (2013.01); *A61B 8/0891* (2013.01); *A61B 8/14* (2013.01); *A61B 8/463* (2013.01)

(56) References Cited

U.S. PATENT DOCUMENTS

2005/0165308 A1    7/2005  Jacob et al.
2009/0187100 A1*   7/2009  Sengupta ............ A61B 5/0275
                                                 600/431

FOREIGN PATENT DOCUMENTS

| JP | 7-241291 A    | 9/1995  |
| JP | 7-303641 A    | 11/1995 |
| JP | 9-131346 A    | 5/1997  |
| JP | 2005-514997 A | 5/2005  |
| JP | 2006-75426 A  | 3/2006  |

OTHER PUBLICATIONS

International Search report from International Application No. PCT/JP12/69599 mailed Oct. 30, 2012.
Angelsen et al, Estimation of Regurgitant Volume and Orifice in Aortic Regurgitation Combining CW Doppler and Parameter Estimation in a Windkessel-like Model, IEEE Transactions on Biomedical Engineering, Oct. 1990, vol. 37, No. 10 pp. 930-936.

* cited by examiner

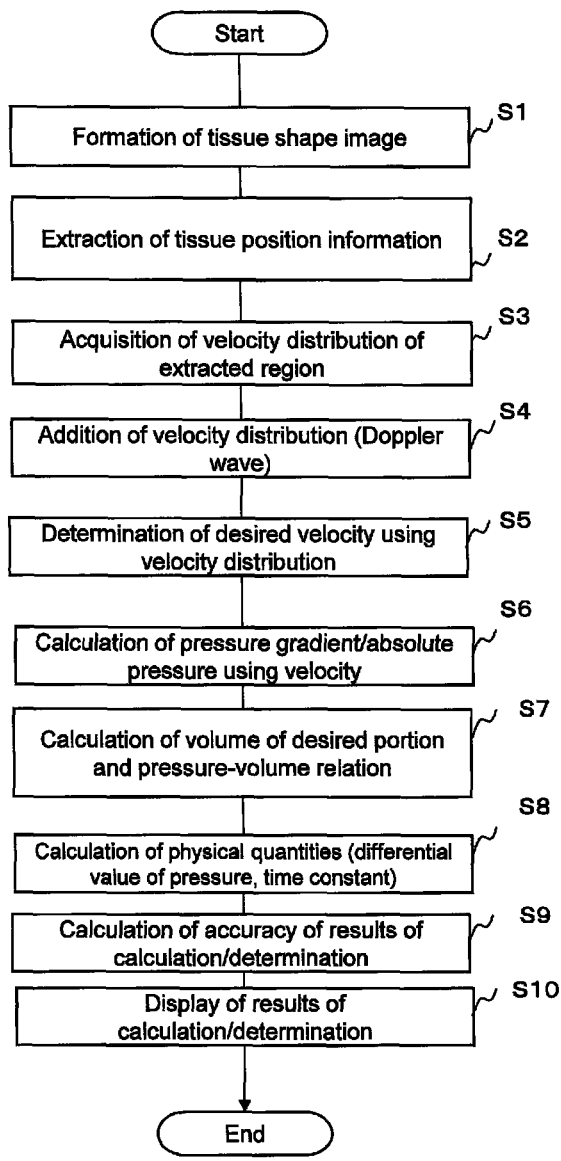

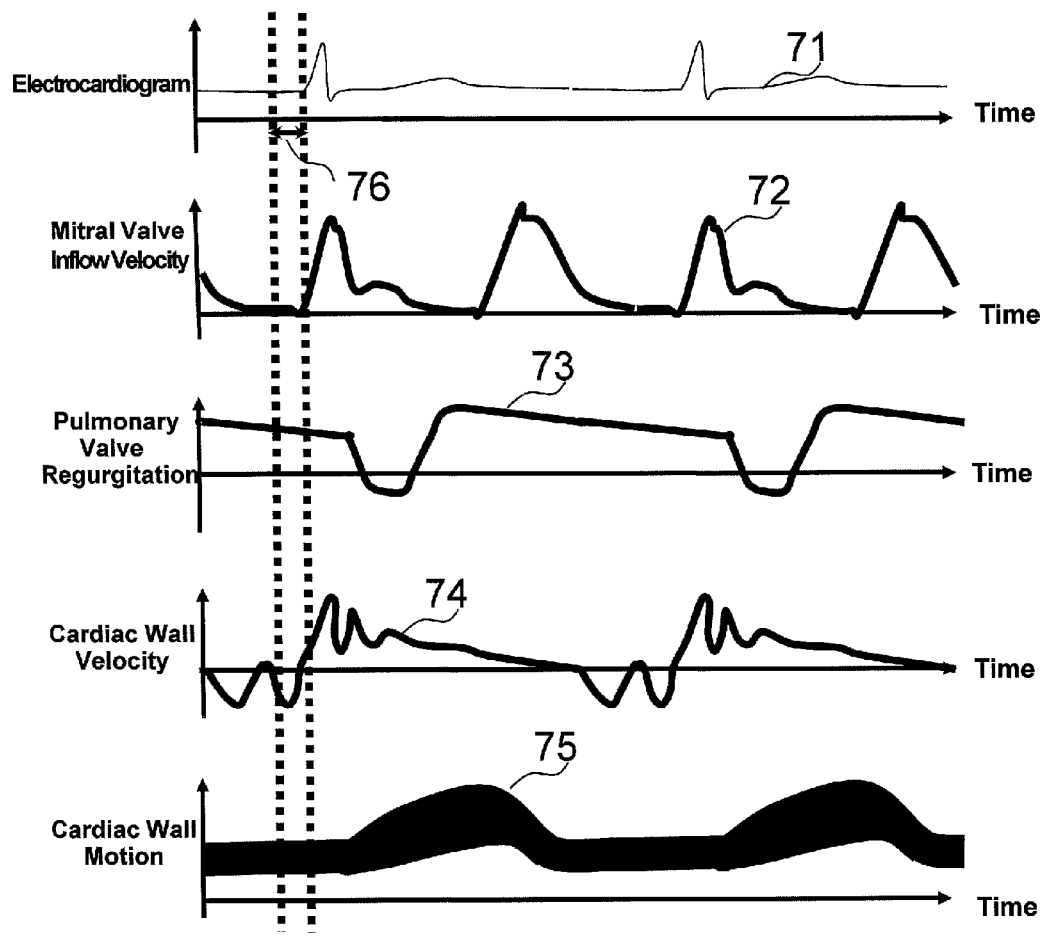

FIG.9
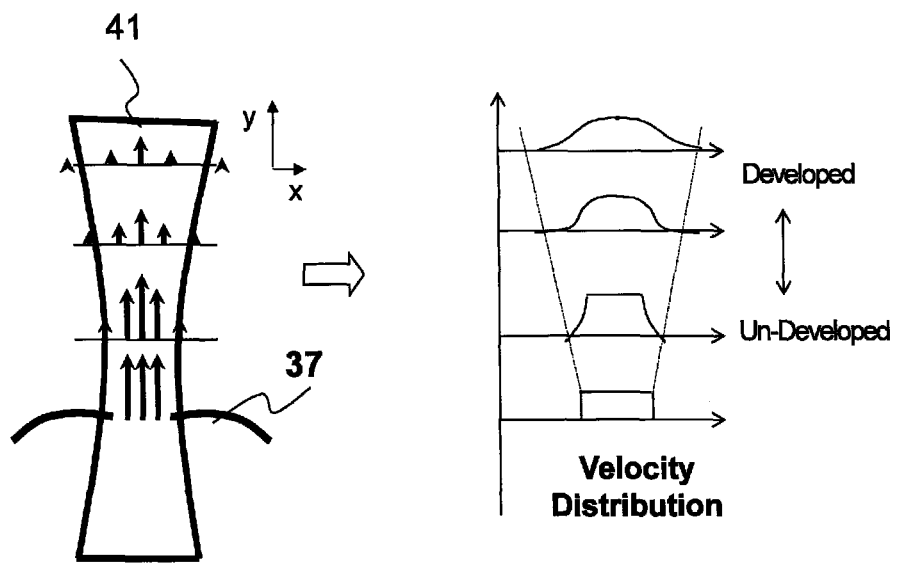
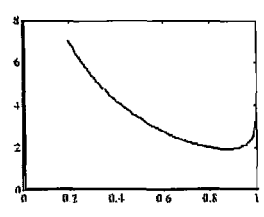
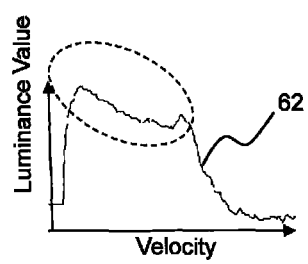
FIG.10A   FIG.10B

ULTRASOUND IMAGING EQUIPMENT AND METHOD

TECHNICAL FIELD

The present invention relates to an ultrasound imaging apparatus and ultrasound imaging method for medical use, especially an ultrasound imaging apparatus enabling sufficiently accurate measurement of blood flow velocity, which is desired by testers.

BACKGROUND ART

In the circulatory system for circulating blood in the bodies, the blood circulation efficiency and pattern closely relate to cardiovascular diseases. For example, an inefficient circulatory system imposes a load on the heart to increase the risk of cardiac failure. In order to investigate such hemodynamics, it is necessary to accurately obtain cardiac blood flow velocity. In particular, the pressure gradient for two points in the living body as important information for diagnosis is obtained by using valve regurgitation flow velocity, and therefore accurate flow velocity information focused on the valve regurgitation is required.

There is the Doppler measurement technique utilizing the Doppler effect as a method for obtaining blood flow velocity using ultrasonic waves. In the Doppler measurement technique, blood flow velocities are detected in all the regions irradiated with ultrasonic waves, and therefore the obtained velocity information (blood flow velocity distribution and blood flow velocity) has a certain width (range). Therefore, it is necessary to extract velocity information considered by a tester to be appropriate, but such extraction of velocity includes ambiguity, which leads to ambiguity of diagnosis.

Patent documents 1 and 2 disclose techniques for preventing errors of trace lines of Doppler waveform due to noises or signal aliasing in determining velocities on the basis of the Doppler waveform. Further, Patent document 3 discloses a technique of automatic tracing of the Doppler waveform utilizing a plurality of luminance levels lower than the maximum luminance level by predetermined degrees as the tracing levels, as for the basis of tracing of the Doppler waveform.

PRIOR ART REFERENCES

Patent Documents

Patent document 1: Japanese Patent Unexamined Publication (KOKAI) No. 7-241289
Patent document 2: Japanese Patent Unexamined Publication (KOKAI) No. 7-241291
Patent document 3: Japanese Patent Unexamined Publication (KOKAI) No. 7-303641

DISCLOSURE OF THE INVENTION

Object to be Achieved by the Invention

Although the above techniques improve the reproducibility of the velocity determination, they arbitrarily determine the trace level of the trace line for determining the velocity, and therefore physical appropriateness of the value calculated as the velocity cannot be secured. Accordingly, high order physical quantities obtained by using the blood flow velocity, such as pressure gradient, become more indefinite.

Therefore, an object of the present invention is to eliminate ambiguity of the velocity distribution information obtained by the Doppler measurement and thereby determine blood flow velocity value desired by testers with good accuracy.

Means for Achieving the Object

The ultrasound imaging apparatus of the present invention that achieves the aforementioned object estimates a model describing physical phenomena including velocity for blood flow as the object of the velocity information desired by testers, and determines velocity information consistent with the estimated model of the blood flow from actually measured velocity distribution information of a measurement region.

That is, the ultrasound imaging apparatus of the present invention comprises an ultrasound probe for transmitting ultrasonic waves to a test subject and receiving echo signals reflected by the test subject, a signal processing part for processing the echo signals received by the ultrasound probe, and a display part for displaying processing results obtained by the signal processing part, wherein the signal processing part comprises a velocity distribution acquisition part for acquiring velocity distribution of a fluid contained in the test subject from the echo signals, and a velocity determination part for determining velocity information from the velocity distribution acquired by the velocity distribution acquisition part, and the velocity determination part sets a model of the velocity information, and determines the velocity information so that the model and the velocity distribution acquired by the velocity distribution acquisition part are consistent with each other.

In the ultrasound imaging apparatus of the present invention, for example, the velocity determination part estimates spatial distribution of the velocity of the fluid as the model, determines the estimated spatial distribution of the velocity so that it is consistent with the velocity distribution acquired by the velocity distribution acquisition part, and calculates the velocity information from the determined spatial distribution of the velocity. Alternatively, the velocity determination part sets a model expressed with a sum of a step function and a delta function as the model of the velocity information of the fluid, and calculates the velocity information by using a value of a singular point of the velocity distribution acquired by the velocity distribution acquisition part.

Further, the ultrasound imaging method of the present invention is an ultrasound imaging method for obtaining diagnostic information of a test subject by using echo signals reflected by the test subject irradiated with ultrasonic waves, which comprises the step of obtaining velocity distribution of a fluid contained in the test subject using the echo signals, and the step of determining velocity information from the velocity distribution of the fluid, wherein the step of determining the velocity information comprises the step of setting a model of the velocity information, the step of searching the velocity distribution of the fluid for a velocity consistent with the model, and determining it, and the step of displaying the determined velocity and/or diagnostic information calculated from the velocity.

In the ultrasound imaging method of the present invention, the diagnostic information calculated from the velocity includes, for example, any of pressure gradient, absolute pressure, time differential value of pressure, time constant, and pressure-volume relation diagram.

Effect of the Invention

According to the present invention, accuracy of the Doppler measurement is improved, and accuracy of calculation concerning pressure, which has been conventionally bad, is thereby improved.

BRIEF DESCRIPTION OF THE DRAWINGS

FIG. 2 is a flowchart showing operation of the signal processing part according to the first embodiment.

FIG. 7 is a drawing for explaining synchronized signals in the case of synchronized imaging.

FIG. 9 is a drawing for explaining jet as an object of imaging.

FIG. 10A is a drawing for explaining the fitting according to the first embodiment, which shows calculated values of a luminance value-velocity distribution.

FIG. 10B is a drawing for explaining the fitting according to the first embodiment, which shows actually measured values of the same.

MODES FOR CARRYING OUT THE INVENTION

The ultrasound imaging apparatus of the present invention comprises an ultrasound probe for transmitting ultrasonic waves to a test subject and receiving echo signals reflected by the test subject, a signal processing part for processing the echo signals received by the ultrasound probe, and a display part for displaying processing results obtained by the signal processing part. The signal processing part comprises a velocity distribution acquisition part for acquiring velocity distribution of a fluid contained in the test subject from the echo signals, and a velocity determination part for determining velocity information from the velocity distribution acquired by the velocity distribution acquisition part. The velocity determination part sets a model of velocity information, and determines the velocity information so that the model and the velocity distribution acquired by the velocity distribution acquisition part are consistent with each other.

Specifically, the velocity determination part estimates spatial distribution of the velocity of the fluid as the model, determines the estimated spatial distribution of the velocity so that it is consistent with the velocity distribution acquired by the velocity distribution acquisition part, and calculates the velocity information from the determined spatial distribution of the velocity. Alternatively, the velocity determination part sets a model expressed with a sum of a step function and a delta function as the model of the velocity information of the fluid, and calculates the velocity information by using a value of a singular point of the velocity distribution acquired by the fluid velocity distribution acquisition part.

Hereafter, embodiments of the present invention will be explained with reference of the drawings.

Figure 1A:
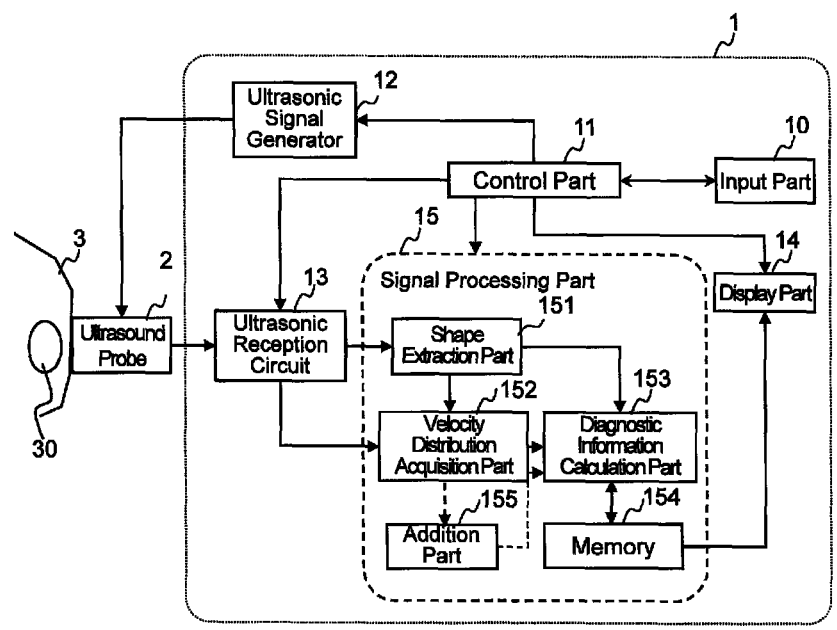
FIG. 1A is a block diagram showing the apparatus configuration of the ultrasound imaging apparatus according to one embodiment of the present invention, which is a block diagram of the whole apparatus.
Figure 1B:
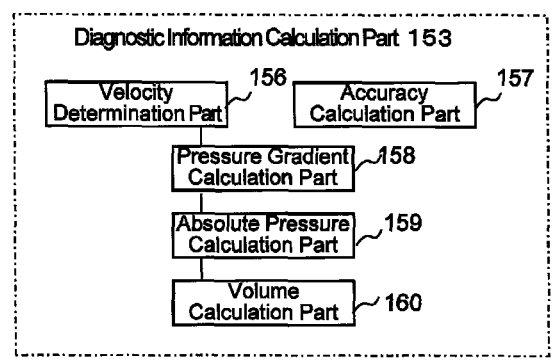
FIG. 1B is a block diagram showing the apparatus configuration of the ultrasound imaging apparatus according to one embodiment of the present invention, which is a block diagram of the diagnostic information calculation part.

FIG. 1 includes block diagrams showing an example of the apparatus configuration of the ultrasound imaging apparatus according to the present invention. FIG. 1A shows the whole apparatus, and FIG. 1B shows the details of the diagnostic information calculation part as a part of the signal processing part. As shown in FIG. 1A, the ultrasound imaging apparatus of this embodiment has a body 1 of the apparatus, and an ultrasound probe 2.

The body 1 of the apparatus is used for generating an ultrasonogram with controlling the ultrasound probe 2, and comprises an input part 10, a control part 11, an ultrasonic signal generator 12, an ultrasonic reception circuit 13, a display part 14, and a signal processing part 15.

The ultrasound probe 2 is contacted with a living body (subject) 3, irradiates ultrasonic waves on an irradiation region 30 according to signals generated by the ultrasonic signal generator 12, and receives reflected wave echo signals of the irradiation region 30. The ultrasound probe 2 generates continuous waves or pulse waves according to the scanning scheme.

Each of the components of the body 1 of the apparatus will be explained. The input part 10 has a keyboard and a pointing device for a tester operating the ultrasound imaging apparatus to set operation conditions of the ultrasound imaging apparatus at the control part 11, and when an electrocardiogram is used, it also functions as an electrocardiogram signal input part.

The control part 11 controls the ultrasonic signal generator 12, the ultrasonic reception circuit 13, the display part 14, and the signal processing part 15 according to the operating conditions of the ultrasound imaging apparatus set from the input part 10, and it consists of, for example, CPU of a computer system.

The ultrasonic signal generator 12 comprises an oscillator for generating signals of a predetermined frequency, and sends a drive signal to the ultrasound probe 2. The ultrasonic reception circuit 13 performs signal processings such as amplification and phasing of the reflected echo signals received by the ultrasound probe 2. The ultrasonic reception circuit 13 includes a reception circuit, an envelope demodulation means, and a means for performing log compression. The display part 14 outputs the information acquired by the signal processing part 15. The signal processing part 15 has a function of generating an ultrasonogram from the reflected echo signals sent from the ultrasound probe 2. The details thereof will be described later.

Although not shown in the drawing, the body 1 of the apparatus further comprises a scan converter and an A/D converter. The scan converter may be included in the ultrasonic reception circuit 13, or provided downstream of the signal processing part 15. When the ultrasonic reception circuit 13 includes a scan converter, there is obtained an advantage that amount of data dealt by the signal processing part 15 is reduced. Further, when a scan converter is not included in the ultrasonic reception circuit 13, a lot of data can be dealt by the signal processing part 15, and thus an accurate measurement apparatus can be realized. The A/D converter is provided upstream of the signal processing part 15. The sampling frequency thereof is usually set to be 20 to 50 MHz.

The details of the constituents of the signal processing part 15 will be explained below. The signal processing part 15 has a shape extraction part 151, a velocity distribution acquisition part 152, a diagnostic information calculation part 153 for calculating velocity information, a memory 154, and an addition part 155 as major constituents concerning the present invention. The diagnostic information calculation part 153 comprises a velocity determination part 156 for determining velocity, an accuracy calculation part 157 for calculating accuracy of processing results obtained by the diagnostic information calculation part 153, and calculation parts 158 to 160 for calculating various kinds of diagnostic information including pressure gradient, absolute pressure, pressure-volume curve, and so forth on the basis of the velocity, as shown in FIG. 1B.

The shape extraction part 151 forms, for example, a B-mode image, namely, a two-dimensional tissue shape image obtained by using a plane imaging method for an object of the ultrasonic irradiation, or a three-dimensional tissue shape image obtained by using a volume imaging method, from the reflected echo signals outputted from the ultrasonic reception circuit 13. Further, the shape extraction part 151 extracts tissue position information from the tissue shape image. The velocity distribution acquisition part 152 extracts blood flow information of a predetermined position acquired from tissue shape information. The velocity determination part 156 determines velocity information desired by a tester from the blood flow information. The memory 154 memorizes the reflected echo signals and information retained by the shape extraction part 151, the velocity distribution acquisition part 152, and the diagnostic information calculation part 153.

Further, the ultrasound imaging apparatus of this embodiment comprises a cycle information acquisition part (input part 10) for acquiring cardiac cycle information (electrocardiogram or phonocardiogram) of a test subject, and the velocity distribution acquisition part 152 obtains the velocity distribution for every cardiac cycle on the basis of the cardiac cycle information obtained by the cycle information acquisition part. The addition part 155 adds the velocity distributions obtained for every cardiac cycle by the velocity distribution acquisition part 152. The velocity determination part 156 can determine velocity information by using the added velocity distribution.

The accuracy calculation part 157 calculates accuracy of the velocity information calculated by the velocity determination part 156 and/or the diagnostic information calculated from the velocity information. The accuracy calculation part 157 calculates the accuracy (index) by using, for example, difference of a local maximum and a local minimum in the velocity distribution acquired by the velocity distribution acquisition part. The pressure gradient calculation part 158 calculates a pressure gradient between the inside and outside of a valve by using the velocity information on valve regurgitation flow determined by the velocity determination part 156. The absolute pressure calculation part 159 calculates an absolute pressure from the pressure gradient calculated by the pressure gradient calculation part 158 and a standard pressure set beforehand or externally inputted. The volume calculation part 160 calculates, for example, volume of a desired organ, for example, the left ventricle, at a plurality of time points from the shape image formed by the shape extraction part 151. The signal processing part 15 may further have a means for calculating a time differential value (dP/dt) and/or a time constant τ of an exponential function used at the time of approximating a relaxed state of the left ventricle, from an absolute pressure of the left ventricle calculated by the absolute pressure calculation part 159.

On the basis of the configuration of the apparatus explained above, embodiments of the operation of the ultrasound imaging apparatus will be explained. In the following embodiments, velocity information is velocity information of valve regurgitation flow of the heart, and the velocity determination part uses a jet model as the model of velocity information. The velocity determination part creates this jet model by a convolution operation with a model of a jet-developed region and a model of a jet-undeveloped region.

The process flow of this embodiment is shown in FIG. 2. FIG. 2 shows a flow for a case where a site including the aortic valve and the left ventricle is the irradiation region 30 mentioned in FIG. 1, as a specific example. However, the irradiation region 30 may be a blood vessel or another heart chamber desired by a tester.

First Embodiment

Step S1

First, imaging is performed in order to acquire shape information of the irradiation region (B-mode image). The ultrasonic frequency of the B-mode image is set in the range of 1 to 20 MHz, which enables the imaging. Further, the frame rate for imaging of a tissue, which moves depending on the heartbeat, should be 20 Hz or higher, with which motions of the heart can be imaged. The shape extraction part 151 forms, for example, a B-mode image, that is, a two-dimensional ultrasonic biological image by using a plane imaging method for an object of the ultrasonic irradiation, or a three-dimensional ultrasonic biological image by using a volume imaging method, from the reflected echo signals outputted from the ultrasonic reception circuit 13. For this image formation, the data for ultrasonic biological image are obtained as time series data.

Figure 3:
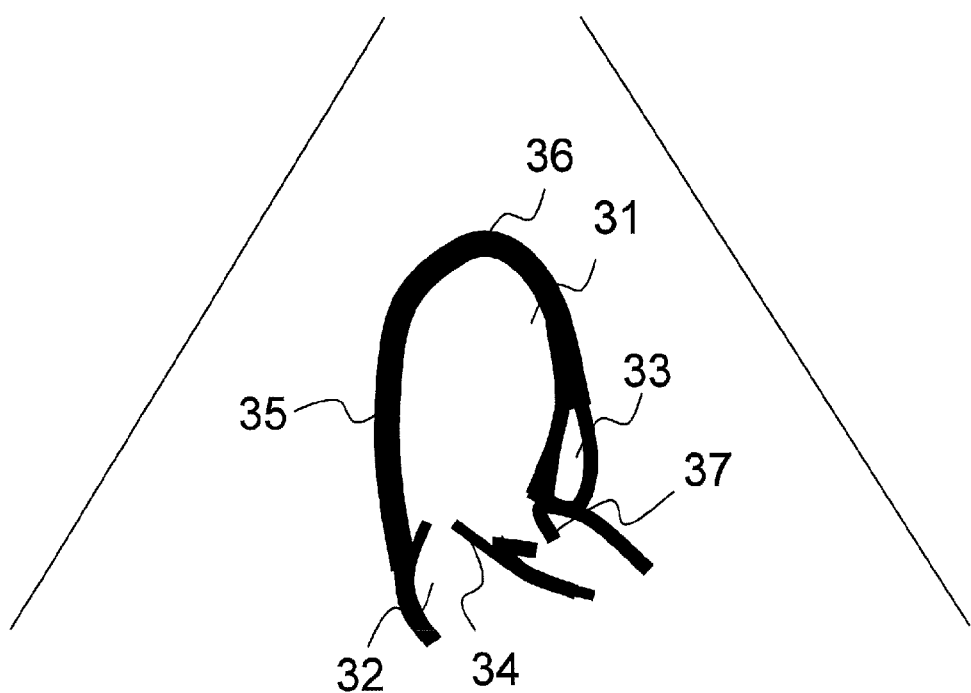
FIG. 3 is a drawing for explaining an object of imaging.

An example of the shape information acquired in Step S1 is shown in FIG. 3. FIG. 3 shows the left ventricle 31, the left atrium 32, the right ventricle 33, the mitral valve 34, the posterior wall 35 of left ventricle, the apex of heart 36, and the aortic valve 37 of the heart imaged in the two-dimensional B-mode.

Step S2

In the shape extraction part 151, tissue position information is obtained from the ultrasonic biological image formed in Step S1. The determination of the tissue position may be performed by detecting inner walls of tissues through image processing, or by obtaining positional information through specification of inner walls by a tester through the input part 10. Specifically, since tissues are recognized as a high luminance value part in ultrasonograms, high luminance value parts are considered as heart tissues to obtain a two-dimensional or three-dimensional heart tissue position. Alternatively, the position may be given by a tester thorough specification of the inner walls as interface of blood and tissues with a pointing device provided in the input part 10.

Step S3

Then, the velocity distribution acquisition part 152 is focused on a blood flow part in the ultrasonic biological image obtained by the shape extraction part 151 to obtain velocity distribution information (Doppler waveform) of the blood flow part (all or a part of the ultrasonic wave irradiation region).

The blood flow part may be a part through which a blood vessel runs, and is chosen according to the object of diagnosis. As the blood flow part, concerning the pathway via the left ventricle, there can be mentioned, for example, a blood flow flowing from the pulmonary vein into the left atrium, a blood flow flowing from the left atrium to the left ventricle, a regurgitating flow at the mitral valve, an ejection flow from the left ventricle to the aorta, an aortic regurgitation flow, and so forth, and concerning the pathway via the right ventricle, there can be similarly mentioned a flow flowing from the vena cava to the right atrium, a flow flowing from the right atrium into the right ventricle, a tricuspid regurgitation flow, an ejection flow from the right ventricle to the pulmonary artery, a pulmonary valve regurgitation flow, and so forth. This embodiment will be explained by exemplifying an aortic regurgitation flow having abundant blood flow information as the blood flow part. Position of the blood flow part can be detected by image processing on the basis of the tissue image obtained in Step S2, and the aforementioned desired blood flow part is set at this position.

Figures 4A, 4B:
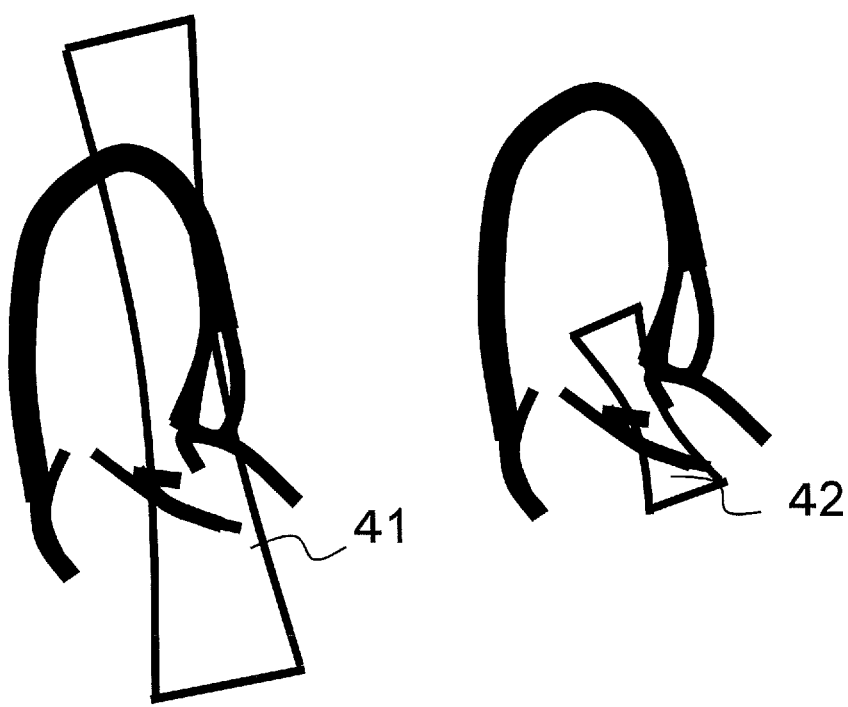
FIG. 4A is a drawing for explaining an imaging region.
FIG. 4B is a drawing for explaining an imaging region.

After setting the part, the measurement is performed for the set part as the object of the measurement by the continuous wave Doppler method or the pulse Doppler method. Although both the continuous Doppler method and the pulse Doppler method can be used for the measurement, the continuous Doppler method that can cover a wide velocity range is used for this embodiment, since the object of this embodiment comprises the mitral valve. As shown in FIG. 4A, the measurement region 41 of the continuous wave Doppler method corresponds to the whole beam region, whereas the measurement region 42 of the pulse Doppler method shown in FIG. 4B is a smaller region.

Figure 5A:
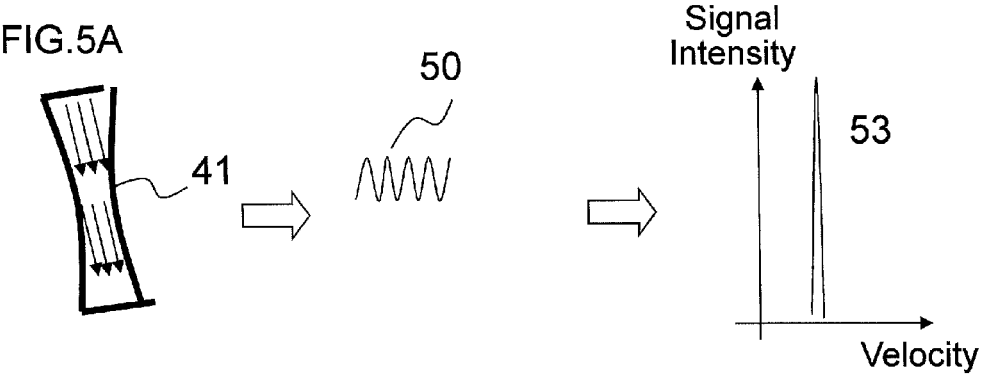
FIG. 5A is a drawing for explaining concept of velocity measurement, which is for a case where velocity in a region is constant.
Figure 5B:
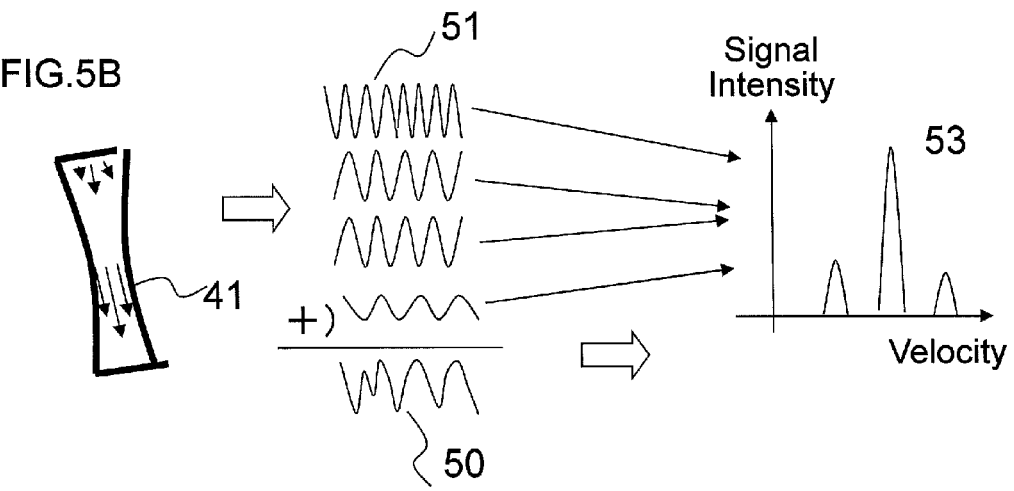
FIG. 5B is a drawing for explaining concept of velocity measurement, which is for a case where various velocities are included in a region.

In both cases, the blood flows in the measurement regions 41 and 42 are not uniform, and have various blood flow velocities. Therefore, the frequency of the ultrasonic waves irradiated by the ultrasonic probe 2 changes depending on the blood flow velocity, and the frequency of the ultrasonic waves detected by the ultrasonic probe 2 include various modulations according to the blood flow velocities in the measurement region. The velocity distribution acquisition part 152 calculates blood flow velocities on the basis of the variation of the ultrasonic wave frequency detected by the ultrasonic probe 2. The outline of the blood flow velocity calculation is shown in FIG. 5. FIG. 5A shows that for the case where blood flows at a uniform velocity in the measurement region 41. In this case, the velocity can be obtained by conducting frequency analysis, such as the Fourier transform, for a modulation signal 50 received by the ultrasound probe 2. FIG. 5B shows the same for the case where there are blood flows of various velocities in the measurement region 41, and the modulation signal 50 received by the ultrasound probe 2 is the total of modulation signals 51 reflecting individual scatterer velocities in blood. By performing frequency analysis for the modulation signal 50, velocity distribution 53 showing the relation between velocity and signal intensity can be obtained. In this case, the signal intensity corresponds to the amount of scatterers having the same velocity.

Figure 6A:
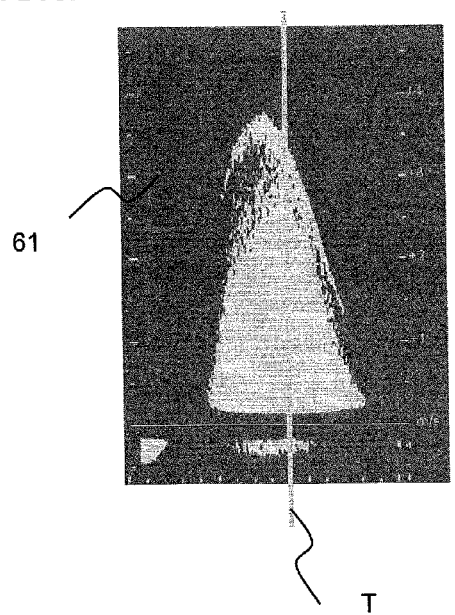
FIG. 6A is a drawing for explaining an image obtained by the velocity distribution acquisition part, which is a Doppler waveform chart.
Figure 6B:
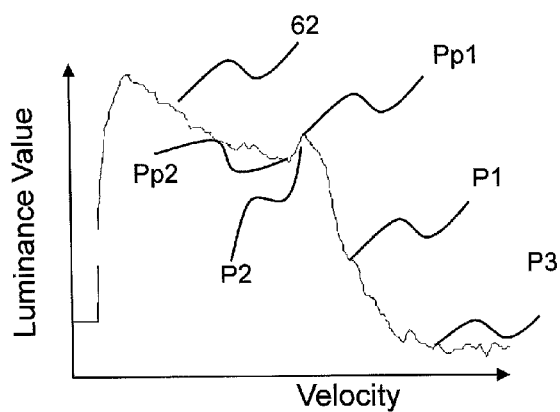
FIG. 6B is a drawing for explaining an image obtained by the velocity distribution acquisition part, which is a luminance value-velocity distribution diagram.
Figure 6C:
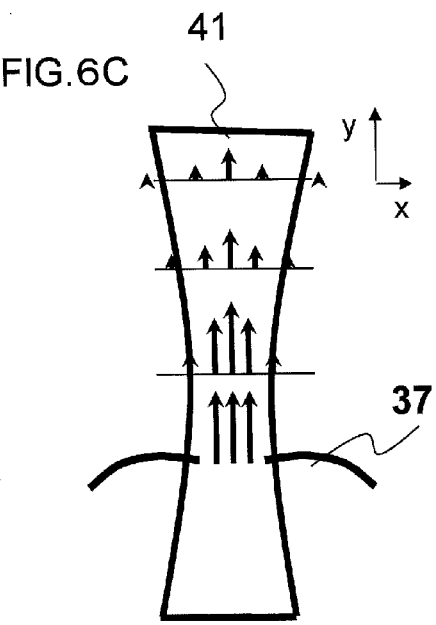
FIG. 6C is a drawing for explaining an image obtained by the velocity distribution acquisition part, which shows an ultrasonic wave irradiation region.

An example of actual velocity distribution information generated by the velocity distribution acquisition part 152 is shown in FIG. 6. FIG. 6A shows a valve regurgitation waveform (Doppler waveform) obtained by continuous wave Doppler method, and is an experimental result obtained by actually opening and closing the aortic valve of a hog with motor driving. The vertical axis indicates the velocity of valve regurgitation flow, and the horizontal axis indicates the time phase. FIG. 6B is a graph showing a curve 62 representing the relation of the velocity and the luminance value of the Doppler waveform 61 at a predetermined time T (luminance value-velocity distribution), where the vertical axis indicates the luminance value, and the horizontal axis indicates the velocity. This curve 62 corresponds to the real data of the signal intensity distribution 53 of the velocity shown in FIG. 5B. FIG. 6C shows the ultrasonic wave irradiation region 41 in the case where the valve flow at the aortic valve 37 is the object.

<Step S4>

For obtaining the velocity distribution information, the velocity distribution acquisition part 152 preferably performs average addition of the Doppler waveforms. Accuracy can be thereby improved. The average addition may be performed by inputting timings of an electrocardiogram or phonocardiogram from the input part 10, or on the basis of cross correlation with respect to the Doppler waveforms by image processing. Various physical quantities as shown in FIG. 7 can be used for detection of the cardiac time phase. FIG. 7 shows changes of an electrocardiogram signal waveform 71, a mitral valve inflow velocity waveform 72, a pulmonary valve regurgitation waveform 73, a cardiac wall velocity waveform 74, and a cardiac wall motion waveform 75, from the top. When an electrocardiogram signal is used, heartbeat time phases based on the electrocardiogram signal waveform 71 inputted from the input part 10 can be recognized. The other waveforms 72 to 75 can be obtained by the Doppler measurement or from M-mode images measured over time, and a specific time phase 76 can be detected on the basis of local maximum, local minimum, maximum value, minimum value, inclination, zero crossing, etc. in the waveforms.

Step S5

The velocity determination part 156 determines the blood flow velocity desired by a tester in consideration of physical consistency from the tissue position information obtained by the shape extraction part 151 in Step S2, and the velocity distribution information obtained by the velocity distribution acquisition part 152 in Step S3 (S5).

Specifically, the relation of the luminance value and the velocity distribution shown in FIG. 6B indicates volume of blood having a certain blood flow velocity existing in a measurement region, therefore a special distribution model of velocity is first supposed for the valve regurgitation, volume of blood having a certain flow velocity u is estimated from the velocity special distribution, and the relation between the velocity u and volume V (u), i.e., the velocity-volume relation, is estimated. Then, by using the correlation of the signal intensity with the volume, the luminance value-velocity relation is estimated from the velocity-volume relation. Finally, the actually measured luminance value-velocity relation and the estimated luminance value-velocity relation are adjusted to obtain a desired velocity U.

Figure 8:
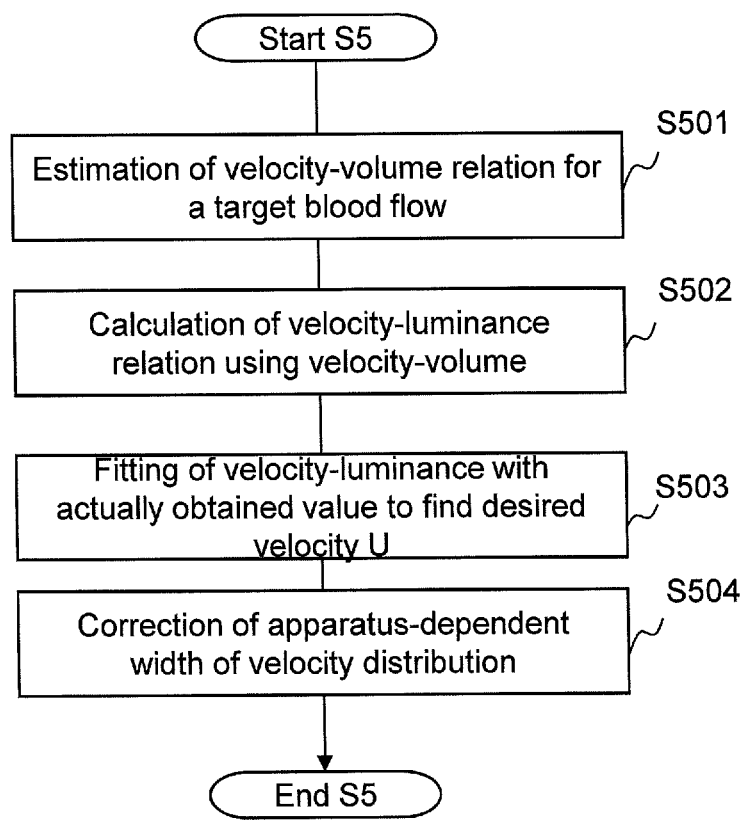
FIG. 8 is a flowchart showing the details of Step S5 mentioned in FIG. 2.

Hereafter, the details of Step S5 will be explained with reference to the flow shown in FIG. 8.

<<Step S501>>

First, for a target blood flow, volume of blood having a certain velocity u is estimated from the model of the spatial distribution of velocity to estimate the relation between the velocity u and the volume V (u). Since the aortic valve regurgitation flow is used as the target in this explanation, the aortic valve regurgitation flow is regarded as a jet for prediction of velocity distribution. In the velocity distribution of aortic valve regurgitation jet, as shown in FIG. 9, the velocity at the center section (core) is outstandingly high in the vicinity of the aortic valve 37, and there are discontinuous changes at the boundaries with the circumference parts, but at positions remote from the aortic valve 37, the velocity change becomes smooth around the core, and the velocity comes to continuously change from the core to the circumference parts. The region showing smooth velocity change at the core region (flat part) is called a region where the jet is developed. In this embodiment, the blood flow is divided into regions where jet is developed or undeveloped around the core, and integration is performed for them with different model equations.

A region where jet is developed (jet-developed region) can be represented by, for example, the following equation (1) known as the Goertler's equation (Non-patent document 1).

[Equation 1]

$$u = \frac{3K}{(8\pi\varepsilon x)\left(1 + \frac{3K}{64\pi\varepsilon^2}\frac{y^2}{x^2}\right)} \quad (1)$$

In the equation, u is a velocity, K is a constant depending on type of jet and relating to momentum of jet, and $\varepsilon$ is a function of K. x is a distance from a virtual starting point of jet along the direction of jet, and y is a distance from the center of jet along the direction perpendicular to jet.

Non-patent document 1: Shagouchi, Jet Engineering (2004) Morikita Shuppan Co., Ltd.

Instead of the equation (1), the Schlichting's equation or the Tollmien's equation may also be used (both are described in Non-patent document 1).

Since the aforementioned equation (1) and the others are effective only for a jet-developed region, a model represented by the equation (2) is used for a jet-undeveloped region.

[Equation 2]

$$u = U\exp\left(-\left(\frac{y}{B}\right)^n\right) \quad (2)$$

In the equation, U is a velocity at the center of jet, and this is the velocity to be obtained in this embodiment. In particular, when pressure gradient between the aorta and the left ventricle is calculated, a velocity near the center of the aortic regurgitation is ideally needed. B is a constant representing smoothness in the core region.

Instead of the equation (2), any of an exponential function, a step function, an error function, and a delta function, or a combination of these may be used.

If a relation expression of volume is obtained by using the aforementioned equations (1) and (2), distribution of volume can be described with the equation (3).

[Equation 3]

$$I(u) = \frac{A}{u}\left(\frac{(CR)^2}{5D}\left(\frac{u}{U}\right)^{-3} + \left(\frac{2B^2}{3n}\right)\left(-\log\frac{u}{U}\right)^{2/n-1}\right) \quad (3)$$

In the equation, R is a radius of the core region, CR is an index representing amplitude of the core region, and C is a constant between 10 and 15. D is a constant automatically derived by an operation, and has a value of 40 to 70.

<<Step S502>>

On the basis of the relation expression of the velocity and the volume calculated in Step S501, relation between the velocity and the luminance value is obtained. This calculation can be realized by obtaining logarithm of the volume in the equation (3), and adding adjustment with a gamma function or the like. The velocity distribution (relation between velocity and luminance value) reproduced by using the equation (3) is shown in FIG. 10A. This result can be considered as favorable reproduction of actually measured values on the basis of comparison with actually measured values 62 (luminance value-velocity distribution) shown again in FIG. 10B as the part indicated with the broken line. In the aforementioned equation (3), A, n, R, σ, and U are unknowns, and are calculated by performing fitting with actually measured values in the following step.

<<Step S503>>

Fitting of the equation of the velocity distribution obtained in Step S502 (equation (3)) and actually obtained values 62 (FIG. 6B) is performed to obtain the unknowns in the equation (3), and the desired velocity U is calculated. As the method for the fitting, known methods such as least square method, least absolute difference method, and pattern matching based on cross correlation can be used. In addition, the fitting may be performed after convolution integration of the equation (3) is performed. In the case of fitting not taking the convolution effect into consideration, convolution effect may be corrected in accordance with the equation (5).

<<Step S504>>

In general, when a Doppler waveform is generated, even if however uniform velocity distribution is measured, it has an apparatus-dependent width, like the velocity distribution 53 shown in FIG. 5. In this step, such an apparatus-dependent width of the velocity distribution is corrected. Specifically, if the characteristic function G of the width is the Gaussian distribution as represented by the equation (4), and the variance thereof is S, for example, the corrected velocity can be represented by the equation (5).

[Equation 4]

$$G = \exp\left(-\left(\frac{u}{S}\right)^2\right) \quad (4)$$

[Equation 5]

$$Uc = U + S \quad (5)$$

In the equation, Uc is the corrected velocity.

Although Step S504 mentioned above is not indispensable for this embodiment, accuracy of the velocity determination can be enhanced by the processing of Step S504.

Steps S501 to S504 explained above are steps performed by the velocity determination part 156. Through these steps, the desired velocity U (after the correction, Uc) is determined.

The diagnostic information calculation part 153 can perform the following Steps S6 to S9 (FIG. 2) by using the velocity U calculated by the velocity determination part 156 as described above to calculate diagnostic information other than the velocity. Among these steps, those chosen by a tester as required may be performed.

Step S6

On the basis of the calculated center velocity U of the aortic regurgitation flow, the pressure gradient dP is obtained in accordance with the simple Bernoulli's equation shown as the equation (6) (processing performed by the pressure gradient calculation part 158). By obtaining pressure gradient for every time phase, information on the time change thereof can be obtained.

[Equation 6]

$$dP = 4U^2 \quad (6)$$

Since the aforementioned pressure gradient is a difference of pressure, and is not absolute pressure, absolute pressure is further calculated by using a standard pressure (processing performed by the absolute pressure calculation part 159). The standard pressure may be a left ventricle absolute pressure $P_{LV}$ which is converted from the standard pressure P inputted from the input part 10. Further, the aorta may be chosen as the standard position for the standard pressure, and the aortic pressure $P_{AO}$ may be chosen as the standard pressure. In this case, a value obtained with an aorta sphygmomanometer can be used as the aortic pressure $P_{AO}$, and the left ventricle absolute pressure $P_{LV}$ is represented by the following equation (7).

[Equation 7]

$$P_{LV} = P_{AO} - dP \quad (7)$$

Step S7

Figure 11:
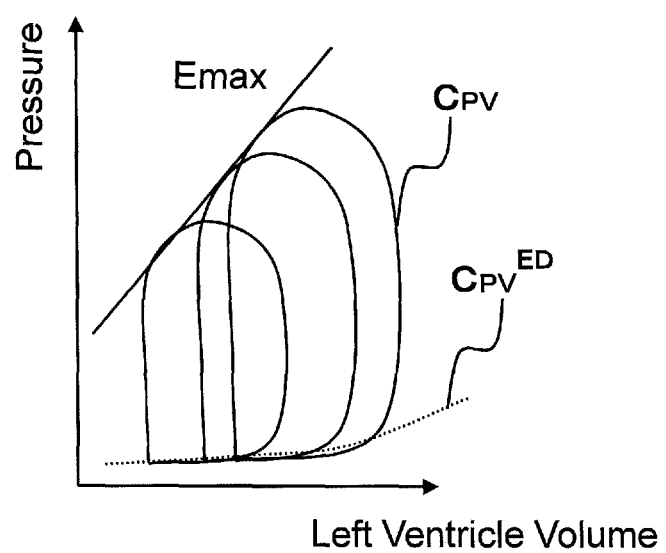
FIG. 11 shows an example of result of operation performed by the signal processing part.

The volume calculation part 160 calculates the volumes of the left ventricle at a plurality of time points from the shape image formed by the shape extraction part 151. For the calculation of the volume of the left ventricle, the Pombo method, the Teichholz method, and so forth may be used, in which the left ventricle is assumed to be a rotation ellipse, and the volume is obtained by using the internal diameter of the left ventricle obtained from a two-dimensional image. Alternatively, by performing three-dimensional imaging of the shape of the heart, the volume can be directly measured. A pressure-volume relation diagram representing the relation between the calculated left ventricle volumes V at a plurality of time points and the absolute pressures P at a plurality of time points calculated in Step S5 is created. An example of the pressure-volume relation diagram is shown in FIG. 11. In the drawing, a plurality of the loop-like curves are pressure-volume relation curves $C_{PV}$ measured for a test subject under different physical conditions, and one heartbeat corresponds to one loop. The different physical conditions mean, for example, conditions before and after imposing a load on the lower extremities, conditions before and after administration of a drug, and so forth. On the basis of such pressure-volume relation curves $C_{PV}$, the inclination $E_{max}$ of the pressure-volume relation at the end systolic phase, or an end diastolic pressure-volume relation curve $C_{PV}^{ED}$ representing the relation between the end diastolic pressure and the volume may be displayed.

The end diastolic pressure $P_{LV}^{ED}$ can be calculated in accordance with the following equation (8).

[Equation 8]

$$P_{LV}^{ED} = P_{AO} - dP^{Op} \quad (8)$$

In the equation, $P_{AO}$ is the aortic pressure from the end diastolic phase to the opening of the aortic valve. Since change of the aortic pressure during a period from the end diastolic phase to the opening of the aortic valve is small, an arbitrary value or average of the aortic pressure during the period from the end diastolic phase to the opening of the aortic valve may be used as $P_{AO}$. Further, $dP^{Op}$ is a pressure gradient between the left ventricle and the left atrium at the time of the aortic valve opening.

Step S8

The diagnostic information calculation part 153 can also calculate dP/dt as a physical quantity representing a time differential value and/or a time constant τ of an exponential function used for approximation of a relaxed state of the left ventricle, from the absolute pressure calculated in Step S6. The values obtained in Steps S6 to S8 serve as important diagnostic indexes representing states of the heart as the test subject.

Step S9

The accuracy calculation part 157 may calculate accuracy of the diagnostic information calculated in the aforementioned steps, especially the velocity determined by the velocity determination part 156. An index of the accuracy can be calculated, for example, in accordance with the following equation (9) by using the value I1 of the extreme of the luminance value $P_{max}$ (Pp1) and the value I2 of the lower extreme of the luminance value $P_{min}$ (Pp2) on the curve 62 shown in the graph of FIG. 6B.

[Equation 9]

$$a = (I1 - I2)/I1 \quad (9)$$

This figure smaller than a certain threshold value indicates that accuracy degrees of the velocity determined in Step S503 or S504, and the various kinds of information calculated in Steps S6 to S8 on the basis of the velocity are low. The calculated index a can be displayed on the display part 14, and a tester can judge whether re-measurement is necessary or not, and so forth by referring it.

The equations (algorithms) of Steps S501 to S504 and Step S6 to S9 described above are stored in the memory part 154 beforehand, and the diagnostic information calculation part 153 such as the velocity determination part 156 reads out them at the time of the calculations of the aforementioned numerical values and performs the calculations.

Step S10

The diagnostic information calculated by the aforementioned diagnostic information calculation part 153 is displayed on the display part 14. The details of the display will be described later.

As explained above, in the ultrasound diagnostic apparatus of this embodiment, a model equation is created for each of the jet-developed region and the jet-undeveloped region of the aortic regurgitation, and fitting of the velocity-luminance value relation expression as the result of the convolution operation of the model equations with actually measured values is performed. A physically consistent velocity can be thereby accurately determined.

Although this embodiment has been explained for the case where the object is an aortic regurgitation flow as a desired blood flow part, this embodiment can be applied not only to the aortic regurgitation flow, but it can also be similarly applied to any blood flow part to which a jet model can be applied.

Second Embodiment

For this embodiment, the configuration of the apparatus is the same as that of the first embodiment (FIG. 1), a B-mode image is first obtained to set a measurement object region, and the Doppler measurement is performed for the set measurement object region similarly to Steps S1 to S4 of the first embodiment. Further, also in this embodiment, the velocity determination part 156 determines a blood flow velocity desired by a tester on the basis of the tissue position information obtained by the shape extraction part 151 and the velocity distribution information obtained by the velocity distribution acquisition part 152 in consideration of physical consistency. In this embodiment, however, the velocity determination part 156 creates an equation for estimating position of the desired velocity in a luminance value-velocity distribution graph of a system including blood flows of a plurality of kinds of different velocities, and applies this equation to an actually measured luminance value-velocity distribution to obtain the desired velocity.

For example, in this embodiment, the velocity determination part sets a model represented with a sum of a step function and a delta function as a model of velocity information, and calculates velocity information by using a value of a singular point of the velocity distribution acquired by the velocity distribution acquisition part. The singular point used by the velocity determination part includes any one of a local minimum, a local maximum, and a point of inflexion of the velocity distribution acquired by the velocity distribution acquisition part.

Figure 12:
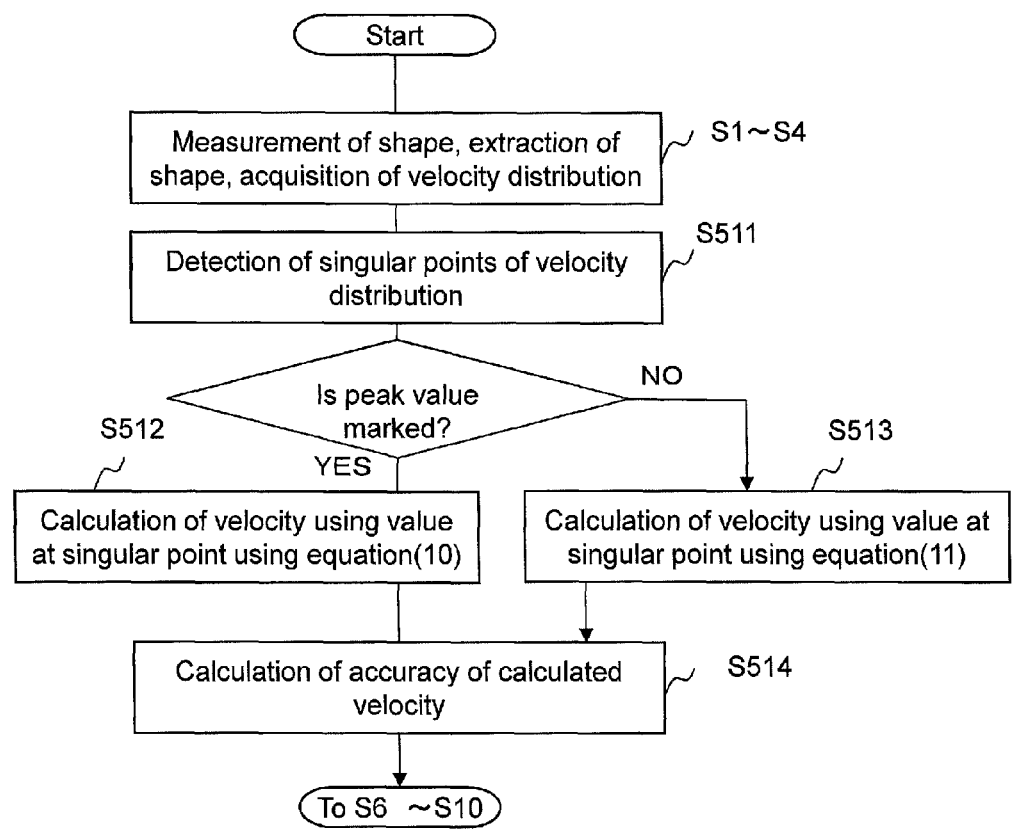
FIG. 12 is a flowchart showing operation of the signal processing part according to the second embodiment.

Hereafter, operations in the second embodiment are explained mainly for the steps different from those of the first embodiment. FIG. 12 is a drawing showing the process flow of the velocity determination part 156 according to the second embodiment, and since Step S1 to S4 and Steps S6 to S10 are the same as those of the first embodiment, explanations thereof are omitted. The details of Step S5 characteristic to this embodiment will be explained below.

<<Step S511>>

The velocity determination part 156 detects a singular point of the velocity distribution information (luminance value-velocity distribution 62 shown in FIG. 6B) obtained by the velocity distribution acquisition part 152. Specifically, the singular point is a luminance value decreasing point of inflexion P1, a luminance value increasing point of inflexion P2, a luminance value extreme Pp (Pp1, Pp2), a luminance lower end P3, or the like. These singular points can be detected from the graph or differentiating the curve. The velocity at the singular point is obtained from the graph, and then the velocity is calculated in the following step S512. When any marked luminance value extreme Pp is not observed, signal intensity of the jet highly possibly decreases, and the process moves to Step S513.

<<Step S512>>

Although the curve of the luminance value-velocity distribution graph includes several characteristic points (singular points) detected in Step S511 such as the luminance lower end P3, the luminance value decreasing point of inflexion P1, the luminance value extreme Pp, and the luminance value increasing point of inflexion P2, the true value of the velocity of the valve regurgitation flow is unknown. Therefore, in this step, it is assumed that the luminance value-velocity distribution is expressed with a sum of a step function and a delta function, and a position where a true value of the velocity at a peak position can be obtained is estimated.

Figure 13A:
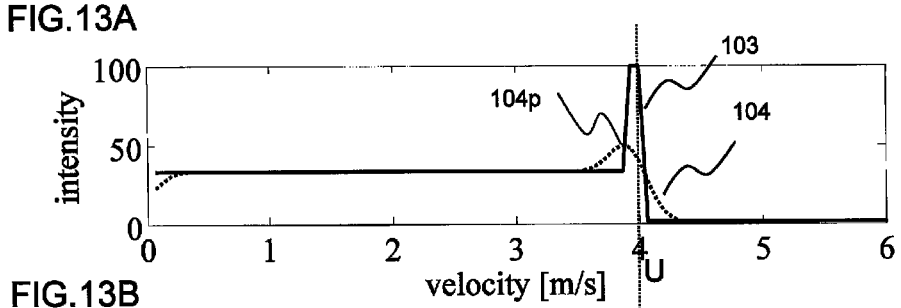
FIG. 13A is a drawing for explaining concept of the second embodiment, which is for a case where there are various velocities.
Figure 13B:
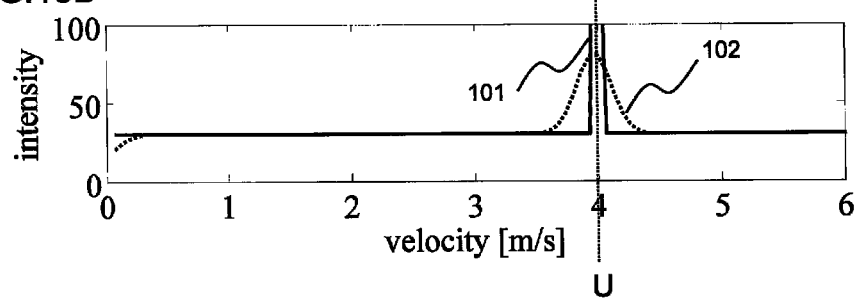
FIG. 13B is a drawing for explaining concept of the second embodiment, which is for a case where velocity is constant.

The concept of the estimation of the velocity position in a velocity-luminance value graph will be explained with reference to FIG. 13. FIG. 13A is for a case where there are a plurality of kinds of velocities, and FIG. 13B is for a case where velocity is constant, in which the horizontal axis indicates the velocity, and the vertical axis indicates the luminance value for both cases. As shown in FIG. 13B, when the blood flow velocity of a measurement region is constant, the luminance value-velocity distribution 101 takes a large value at a velocity U within the range of measured velocity, but it is flattened by the characteristic function G of the apparatus. However, also in the flattened luminance value-velocity distribution 102, there is no change in that the peak of the luminance value exists at the velocity U. On the other hand, in the case where the velocity is constant to a certain extent around the center of the jet, but there are also other velocity components including components of the inverse direction, such a luminance value-velocity distribution 103 as shown in FIG. 13A is observed. Further, when it is flattened by the characteristic function G of the apparatus, a flattened luminance value-velocity distribution 104 is obtained. This luminance value-velocity distribution 104 qualitatively the same as the luminance value velocity distribution 102 in the aspect that there is a peak of the luminance value, but the position of the peak 104$p$ thereof shifts to the lower velocity side from the position of the maximum velocity U in the region. This is because it has been influenced by velocities of the circumference portions. Therefore, it cannot be said that a peak of the luminance value necessarily indicates the velocity at the center of jet.

When the luminance value-velocity distribution 103 is expressed with a sum of a step function and a delta function, the true value U of the velocity at the peak position can be expressed by the following equation (10).

[Equation 10]

$$U = U_1 + U_2 - U_p \quad (10)$$

In the equation, $U_1$ is a value of the velocity at the luminance value decreasing point of inflexion P1, $U_2$ is a value of the velocity at the luminance value increasing point of inflexion P2, and $U_p$ is a value of the velocity at the extreme Pp of the luminance value.

<<Step S513>>

On the other hand, when any marked luminance value extreme Pp does not appear, signal intensity of the jet highly possibly decreases, but it is regarded as a case where the velocity distribution can be assumed with a step function, and the true value U is calculated in accordance with the following equation (11).

[Equation 11]

$$U = U_1 \quad (11)$$

The equation (11) can be applied not only to the aortic regurgitation flow, but also to any flow for which the velocity distribution can be assumed with a step function or the like. For example, an ideal flow in a blood vessel is described by the equation (12), and the frequency function thereof is a kind of step function.

[Equation 12]

$$u = U\left(1 - \left(\frac{r}{R}\right)^2\right) \quad (12)$$

Also in a usual flow in a blood vessel, when the flow in the blood vessel can be measured with sufficient accuracy, it can be described with a similar step function, and thus the equation (11) can be applied.

The method of applying the equations (10) and (11) mentioned above is a convenient method for a case where the luminance value-velocity distribution 103 is expressed with a sum of a step function and a delta function, but the equations (1) and (2) may be used instead of a step function and a delta function. In such a case, the example mentioned in the explanation of step S503 can also be used.

Also in this embodiment, the operation information concerning the velocity determination (equations (10) and (11)) is stored in the memory part 154, and read out by the velocity determination part 156 at the time of the velocity determination.

<<Step S514>>

The accuracy calculation part 157 may calculate accuracy of the velocities determined in Steps S512 and S513 mentioned above by using the information on the luminance value extreme Pp, like Step S9 explained for the first embodiment. The calculated accuracy can be displayed on the display part 14, and a tester can judge whether re-measurement is necessary or not or the like by referring it. Further, various kinds of diagnostic information may be calculated in Steps S6 to S10 by using the determined velocity, as in the first embodiment.

According to this embodiment, the true desired velocity can be determined with a more convenient method compared with the first embodiment in which the desired velocity is calculated by fitting. Further, this embodiment can be applied to any object for which flow of a blood flow can be expressed with a step function. Furthermore, since the function of calculating accuracy of the obtained results is provided in this embodiment, a tester can confirm the accuracy of the determination result.

Embodiments of Display

Although determination of desired velocity and calculation of pressure information using the obtained velocity are mainly explained in the aforementioned embodiments, embodiments of display commonly usable in the aforementioned embodiments will be explained below.

Examples of the graph displayed at the display part 14 are shown in FIG. 14.

Figure 14A:
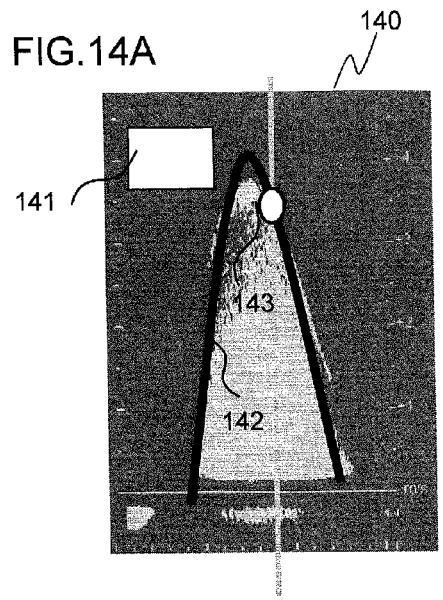
FIG. 14A shows an example of display.

FIG. 14A shows an example where the velocity U at the time phase T desired by a tester is displayed on a screen 140 displaying a Doppler waveform created by the velocity distribution acquisition part 152, and in the example shown in the drawing, the velocity U is displayed as a numerical value in a block 141. Further, on this Doppler waveform, one or more of the luminance value decreasing point of inflexion P1, the luminance value increasing point of inflexion P2, the luminance value extreme Pp, and the calculated velocity U for all or a part of the time phases may be superimposingly displayed as a line 142 formed by connecting them, or as dots 143. Further, in the block 141, the accuracy a of the results of the velocity search may be displayed, or a threshold value is set for the accuracy a, and when a is lower than the threshold value, an indication informing that the measurement accuracy is low may be displayed.

Figure 14B:
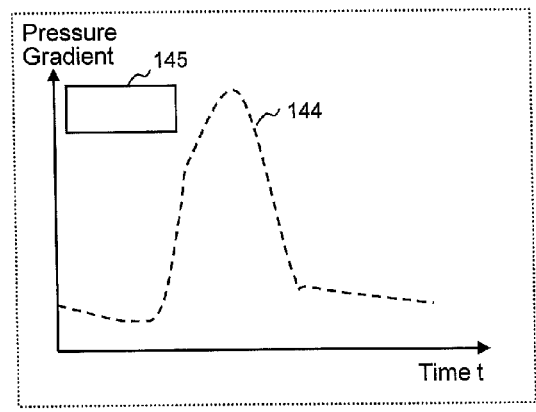
FIG. 14B shows an example of display.

FIG. 14B shows an example where a part or all of the time phases of the pressure gradient dP obtained in Step S6 are displayed. Together with a curve 144 representing the temporal change of the pressure gradient, pressure gradients at one or more time points may be displayed in the block 145.

Figure 14C:
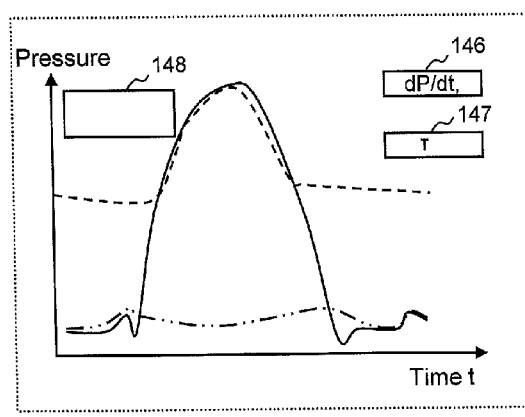
FIG. 14C shows an example of display.

FIG. 14C shows temporal change of the absolute pressures of the parts obtained in Step S7, and in the example shown in the drawing, the solid line indicates absolute pressure in the left ventricle, the broken line indicates absolute pressure in the aorta, and two-dot chain line indicates absolute pressure in the left atrium. Further, when the velocity determination part 156 calculates the time differential value of absolute pressure, dP/dt, and/or the time constant τ of an exponential function used at the time of approximating a relaxed state of the left ventricle, both or either one of dP/dt and τ at time points within all or a part of one heartbeat may be displayed in blocks 146 and 147. Furthermore, advancing state of the processing such as the current step number may be displayed in a box 148.

Figure 14D:
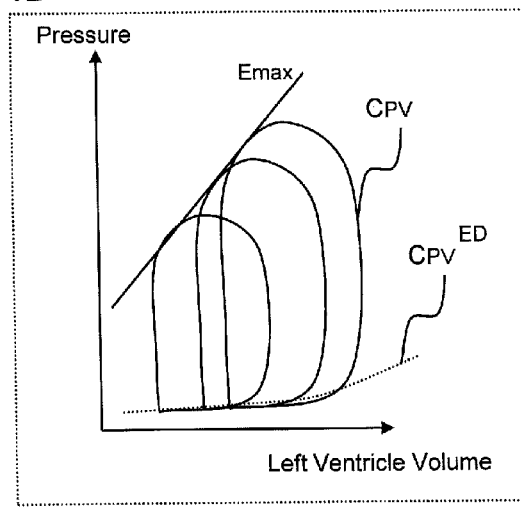
FIG. 14D shows an example of display.

FIG. 14D shows a display of the pressure-volume relation diagram obtained in Step S8. In the pressure-volume relation diagram, in addition to the pressure-volume relation curve $C_{PV}$, the inclination $E_{max}$ of the pressure-volume relation at the end systolic phase, and the end diastolic pressure-volume relation curve $C_{PV}^{ED}$ representing the relation between the end diastolic pressure and the volume may be displayed.

FIG. 14 shows examples of the display, but the display is not limited to the examples of the display shown in FIG. 14, and various modifications are possible. For example, information concerning the absolute pressure may be superimposingly displayed on the tissue image by using the image formed by the shape extraction part 151.

Figure 15:
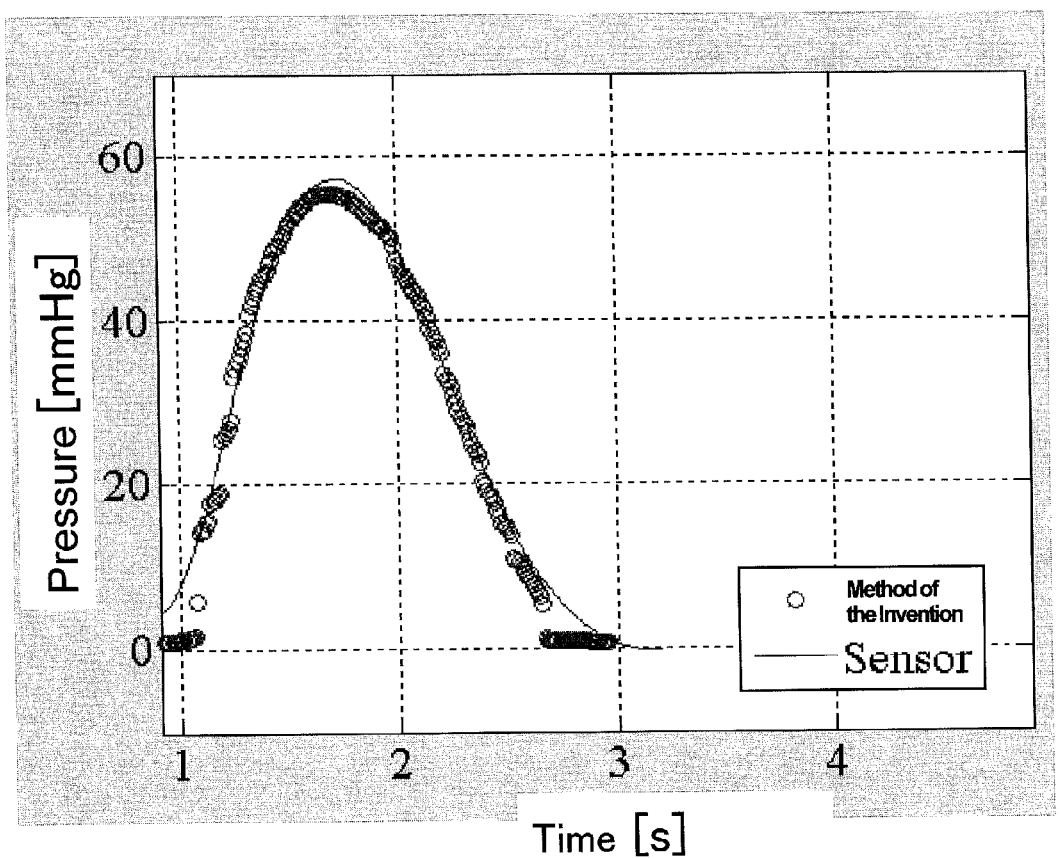
FIG. 15 shows result of measurement of pressure gradient performed by using the method of the second embodiment.

A regurgitation flow velocity measurement was performed by using an apparatus imitating the pig aortic valve, and the pressure gradient was calculated according to the method of the second embodiment of the present invention. The results thereof and the results of comparison of them with results of pressure gradient measurement performed by using a pressure sensor are shown in FIG. 15. In the drawing, the solid line shown in the graph represents the results of the measurement performed by using a pressure sensor, and the circles represent pressures calculated by the method of the second embodiment. As seen from the results shown in FIG. 15, the results obtained by using the method according to the present invention well agreed with the measurement results obtained by using a pressure sensor, and accuracy within several mmHg could be attained by the method of the present invention.

INDUSTRIAL APPLICABILITY

According to the present invention, in ultrasound imaging, a blood flow velocity desired by a tester can be measured with good accuracy, and by using this velocity, information useful for diagnosis, such as pressure gradient and absolute pressure, can be provided as accurate information.

DENOTATION OF REFERENCE NUMERALS

1 . . . Body of apparatus, 2 . . . ultrasound probe, 10 . . . input part, 11 . . . control part, 12 . . . ultrasonic signal generator, 13 . . . ultrasonic reception circuit, 14 . . . display part, 15 . . . signal processing part, 151 . . . shape extraction part, 152 . . . velocity distribution acquisition part, 153 . . . diagnostic information calculation part, 155 . . . addition part, 156 . . . velocity determination part, 157 . . . accuracy calculation part, 158 . . . pressure gradient calculation part, 159 . . . absolute pressure calculation part, 160 . . . volume calculation part

The invention claimed is:

1. An ultrasound imaging apparatus, comprising:
an ultrasound probe configured to transmit ultrasonic waves to a test subject and receiving echo signals reflected by the test subject; and
a computer storing executable functions that cause the ultrasound imaging apparatus to perform:
processing the echo signals received by the ultrasound probe, wherein the echo signals are frequency modulated signals depending on a velocity of a fluid contained in the test subject;
acquiring a Doppler waveform which is a velocity distribution of the fluid from the frequency modulated signals; and
determining a velocity information from the Doppler waveform;
setting a jet model of the velocity information; and
determining the velocity information so that the jet model and the velocity distribution are consistent with each other.

2. The ultrasound imaging apparatus of claim 1, wherein the computer stores further executable functions that cause the ultrasound imaging apparatus to perform:
estimating a spatial distribution of a velocity of the fluid as the jet model,
determining the estimated spatial distribution of the velocity so that it is consistent with the velocity distribution, and
calculating the velocity information from the determined spatial distribution of the velocity.

3. The ultrasound imaging apparatus of claim 1, wherein the velocity information includes velocity information on a valve regurgitation flow of a heart, and wherein the computer stores further executable functions that cause the ultrasound imaging apparatus to perform jet modeling.

4. The ultrasound imaging apparatus of claim 3, wherein the computer stores further executable functions that cause the ultrasound imaging apparatus to perform the jet modeling by a convolution operation of a model of a jet-developed region and a model of a jet-undeveloped region.

5. The ultrasound imaging apparatus of claim 4, wherein the computer stores further executable functions that cause the ultrasound imaging apparatus to perform using any one of: a Goertler's equation, a Schlichting's equation, or a Tollmien's equation as the jet model of jet-developed region.

6. The ultrasound imaging apparatus of claim 4, wherein the computer stores further executable functions that cause the ultrasound imaging apparatus to perform using any one of: an exponential function, a step function, an error function, a delta function, or a function consisting of a combination of the exponential function, the step function, the error function, and the delta function as the jet model of a jet-undeveloped region.

7. The ultrasound imaging apparatus of claim 1, wherein the computer stores further executable functions that cause the ultrasound imaging apparatus to perform:
acquiring a cardiac cycle information of the test subject, and
obtaining the velocity distribution for every cardiac cycle on a basis of the cardiac cycle information.

8. The ultrasound imaging apparatus of claim 7,
wherein the computer stores further executable functions that cause the ultrasound imaging apparatus to perform adding the obtained velocity distribution for every cardiac cycle, and
determining the velocity information by using the added velocity distribution.

9. The ultrasound imaging apparatus of claim 3, wherein the computer stores further executable functions that cause the ultrasound imaging apparatus to perform calculating a pressure gradient of an inside and outside of a valve using the velocity information on the valve regurgitation flow.

10. The ultrasound imaging apparatus of claim 9, wherein the computer stores further executable functions that cause the ultrasound imaging apparatus to perform calculating an absolute pressure from the pressure gradient and a standard pressure set beforehand or externally inputted.

11. The ultrasound imaging apparatus of claim 10, wherein the computer stores further executable functions that cause the ultrasound imaging apparatus to perform calculating a time differential value (dP/dt) and/or a time constant $\tau$ an exponential function used at the time of approximating a relaxed state of the left ventricle, from an absolute pressure of a left ventricle.

12. The ultrasound imaging apparatus of claim 1, wherein the computer stores further executable functions that cause the ultrasound imaging apparatus to perform calculating an accuracy of the velocity information and/or diagnostic information calculated from the velocity information.

13. The ultrasound imaging apparatus of claim 12, wherein the computer stores further executable functions that cause the ultrasound imaging apparatus to perform calculating the accuracy by using a difference of a local maximum and a local minimum of the velocity distribution.

14. The ultrasound imaging apparatus of claim 10, wherein the computer stores further executable functions that cause the ultrasound imaging apparatus to perform:
calculating a volume of a left ventricle from a left ventricle shape, creating a pressure-volume relation diagram by using the left ventricle volume and the absolute pressure of the left ventricle, and making a screen display the created diagram.

15. The ultrasound imaging apparatus of claim 14, wherein the computer stores further executable functions that cause the ultrasound imaging apparatus to perform:

creating the pressure-volume relation diagrams for a plurality of kinds of different conditions, creating, using the plurality of pressure-volume relation diagrams, inclination $E_{max}$ of a pressure-volume relation curve at an end systolic phase and an end diastolic pressure-volume relation curve, and making the screen display the inclination $E_{max}$ of the pressure-volume relation curve at the end systolic phase and the end diastolic pressure-volume relation curve.

* * * * *